United States Patent
Fuhr et al.

(10) Patent No.: US 7,439,075 B2
(45) Date of Patent: Oct. 21, 2008

(54) METHOD AND DEVICE FOR WITHDRAWING SUSPENDED MICROPARTICLES FROM A FLUIDIC MICROSYSTEM

(75) Inventors: Gunter Fuhr, Berlin (DE); Stephen Graham Shirley, Brandon (GB); Torsten Muller, Berlin (DE); Thomas Schnelle, Berlin (DE); Rolf Hagedorn, Berlin (DE)

(73) Assignee: Perkinelmer Cellular Technologies Germany GmbH, Hamburg (DE)

( * ) Notice: Subject to any disclaimer, the term of this patent is extended or adjusted under 35 U.S.C. 154(b) by 653 days.

(21) Appl. No.: 10/203,168
(22) PCT Filed: Feb. 8, 2001
(86) PCT No.: PCT/EP01/01356
§ 371 (c)(1), (2), (4) Date: Oct. 21, 2002
(87) PCT Pub. No.: WO01/58592
PCT Pub. Date: Aug. 16, 2001

(65) Prior Publication Data
US 2003/0108452 A1    Jun. 12, 2003

(30) Foreign Application Priority Data
Feb. 9, 2000   (DE)  ............................ 100 05 735

(51) Int. Cl.
| | |
|---|---|
| G01N 1/10 | (2006.01) |
| G01N 15/06 | (2006.01) |
| G01N 21/00 | (2006.01) |
| G01N 31/00 | (2006.01) |
| G01N 33/00 | (2006.01) |
| G01N 27/26 | (2006.01) |
| B01D 57/02 | (2006.01) |
| B01D 59/42 | (2006.01) |
| B01D 59/50 | (2006.01) |
| B01D 61/42 | (2006.01) |
| B01D 61/58 | (2006.01) |
| G01L 9/18 | (2006.01) |
| G01L 1/20 | (2006.01) |
| G01F 1/64 | (2006.01) |
| C02F 1/469 | (2006.01) |
| C02F 1/40 | (2006.01) |
| C02F 11/00 | (2006.01) |
| C07K 1/26 | (2006.01) |
| C08F 2/58 | (2006.01) |
| C25B 7/00 | (2006.01) |
| C25B 15/00 | (2006.01) |

(52) U.S. Cl. .................. 436/180; 204/450; 204/451; 204/452; 204/453; 204/454; 204/600; 204/601; 204/602; 204/603; 204/604; 204/605; 204/455; 422/68.1; 422/81; 422/100

(58) Field of Classification Search ............... 436/180; 438/180; 204/450–455, 600–605; 422/68.1, 422/81, 100
See application file for complete search history.

(56) References Cited

U.S. PATENT DOCUMENTS
4,343,551 A * 8/1982 Eisert ..................... 377/10
(Continued)

FOREIGN PATENT DOCUMENTS
WO    WO 99/66318    12/1999

OTHER PUBLICATIONS

Gert Blankenstein & Ulrik Larsen, Modular Concept of a Laboratory on a Chip for Chemical and Biochemical Analysis, BioSensors & Bioelectronics, vol. 13 No. 3-4, pp. 427-438, 1998.*

(Continued)

*Primary Examiner*—Jill Warden
*Assistant Examiner*—Keri A Moss
(74) *Attorney, Agent, or Firm*—Caesar, Rivise, Bernstein, Cohen & Pokotilow, Ltd.

(57) ABSTRACT

A method of discharging a fluid flow with suspended microparticles from a fluidic microsystem (10) is described, whereby the fluid flow converges with at least one output flow to form a discharge flow at the end of a discharge channel (14) of the microsystem, and the discharge flow is delivered through a conduction element (19). A microsystem with a flow output device for implementation of this method is also described.

9 Claims, 3 Drawing Sheets

U.S. PATENT DOCUMENTS

| 4,352,558 | A | | 10/1982 | Eisert | |
|---|---|---|---|---|---|
| 6,120,666 | A | * | 9/2000 | Jacobson et al. | 204/452 |
| 6,613,580 | B1 | * | 9/2003 | Chow et al. | 436/180 |
| 6,749,736 | B1 | * | 6/2004 | Fuhr et al. | 204/643 |
| 6,899,137 | B2 | * | 5/2005 | Unger et al. | 137/833 |

OTHER PUBLICATIONS

Radbruch (Ed.), *Flow Cytometry and Cell Sorting*, pp. 8-9, 153-155 and 159-161 (1992).

Blankenstein, "Microfabricated Flow System for Magnetic Cell and Particle Separation," in *Scientific and Clinical Applications of Magnetic Carriers*, pp. 233-245 (Hafali et al, Eds. 1997).

Blankenstein et al., "Modular Concept of a Laboratory on a Chip for Chemical and Biochemical Analysis," in *Biosensors & Bioelectronics* vol. 13, No. 3-4, pp. 427-438 (1998).

\* cited by examiner

METHOD AND DEVICE FOR WITHDRAWING SUSPENDED MICROPARTICLES FROM A FLUIDIC MICROSYSTEM

BACKGROUND OF THE INVENTION

This invention relates to a method of discharging suspended microparticles from a fluidic microsystem, in particular for discharging the microparticles from the microsystem, and a method for metering and/or treating of a microparticle flow output from a fluidic microsystem. This invention also relates to a microsystem designed for controlled discharge of suspended microparticles, and a discharge device for discharging suspended microparticles from a microsystem.

Fluidic microsystems for manipulation of biological or synthetic microparticles are known in general. The microsystems usually include one or more input channels, a channel arrangement for receiving and/or guiding fluids with suspended microparticles (e.g., biological cells) and one or more output channels. The channel arrangement has typical dimensions in the submillimeter range, e.g., approx. 100 to 500 µm. The suspended microparticles are characterized and/or manipulated electrically and/or optically, for example, in the channel arrangement. The suspension liquid with the microparticles has a freely adjustable flow velocity in the channel arrangement, which depends in particular on the manipulation and/or characterization steps implemented. Typical flow velocities are in the range of 10 mm/s or less. In conventional systems, connecting lines (so-called tubing) are connected to the output channels as the ends of the actual microsystem, in which connecting lines the microparticles are discharged from the respective outlet channel for further processing or collection or the like. These connecting lines typically have a length of approx. 2 to 8 cm. This corresponds to approx. 1 to 4 µl at an inner diameter of 254 µm, for example. A cell has essentially the same velocity in a connecting line as in manipulation in the channel arrangement and thus it needs a transit time of approx. 3 to 60 minutes from the outlet of the microsystem to the end of the connecting line, depending on the pump rates.

Such high transit times are unfavorable for reproducible further processing of the suspended microparticles. For example, considerably shorter times of approx. 10 to 60 seconds are needed for confirmed single-cell separation, as required for cloning cells. In addition, sedimentation phenomena which also play a role definitely reduce the cell recovery rate when the transit time is too long.

Rapid and reproducible discharge of suspended microparticles from microsystems, metering and/or treating of the oncoming flow of microparticles in transmission into subsequent systems is a problem that has not previously been solved at a justifiable technical expense.

The so-called enveloping flow principle of hydrodynamic focusing is known in fluid technology. Hydrodynamic focusing permits an alignment of specimen particles and, for certain analytical and preparative tasks, it allows particles and cells to be isolated (see A. Radbruch in *Flow Cytometry and Cell Sorting*, Springer Verlag, Berlin 1992). For implementation of the enveloping flow principle, a fluid flow with the particles is surrounded by an outer enveloping flow in a coaxial nozzle design. The enveloping flow must have a much greater velocity than the fluid flow so that hydrodynamic focusing may take place. The flow velocity of the enveloping flow is typically several thousand times greater than the flow velocity of the fluid. The fluid flow is entrained by the enveloping flow. The use of hydrodynamic focusing is limited to macroscopic laboratory equipment. It is not applicable in microsystem technology because due to the required high velocity of an enveloping flow, the flow conditions in the microsystem would also be influenced upstream relative to the aforementioned nozzle design. However, such an external and non-reproducible interference in flow conditions in the channel arrangement of a microsystem is not desirable.

Figure 7:
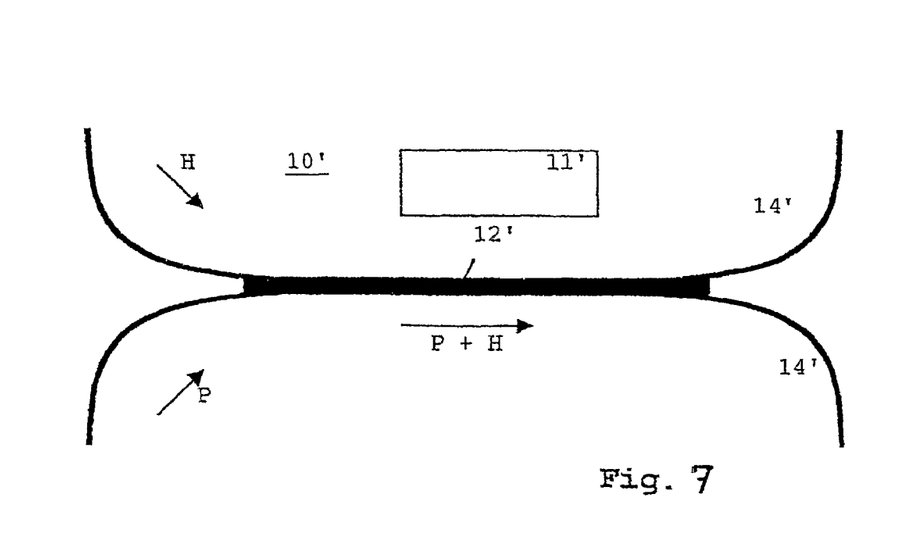
FIG. 7 an illustration of a conventional flow switch in a fluidic microsystem.

Furthermore, there are known microstructured flow switches which are based on the enveloping flow principle (see G. Blankenstein in the publication "Microfabricated flow system for magnetic cell and particle separation" in *Sci. & Clin. Appl. Magn. Carriers*, eds. Häfeli et al., Plenum Press, New York, 1997). With a flow switch 10' a specimen flow P is accompanied by a separate enveloping flow H in the channel arrangement of a microsystem, e.g., in a separation section 12', as illustrated in FIG. 7. A magnetic separation device 11' is provided on separation section 12'. Several outlet channels 14' are connected to the separation section 12', certain fractions of the specimen and enveloping flows being directed into these channels, depending on the function of separation device 11'. Use of the flow switch is limited to fluid convergence flows or fluid separations in the interior of the microsystem. The dimension of the output channels determines the parameters of the specimen and enveloping flows that can be added. The above-mentioned problem of discharging the suspended microparticles from microsystems cannot be solved with a flow switch.

The centering or deflection of a specimen flow is implemented with hydrodynamic focusing and the above-mentioned flow switches. However, the above-mentioned problem of extracting or focusing microparticle suspensions at the outlet of microsystems, i.e., in particular at the interface with macroscopic systems, is not solved in this way.

SUMMARY OF THE INVENTION

The object of the present invention is to provide an improved method and a suitable system for discharging suspended microparticles from a fluidic microsystem, which in particular is robust, has a simple design and guarantees rapid discharge of particles without any negative effect on the function of the microsystem, in particular the flow conditions prevailing there, and can be adapted easily to different applications. This invention attempts in particular to achieve a discharge of microparticles with a fluid flow from microsystems or microcapillary systems with little or no loss of microparticles.

The object of this invention is in particular also to influence the properties of the suspension removed or separated when discharging suspended microparticles. The suspension is to be altered with regard to its physical composition and/or with respect to the particle density (dilution). The object of this invention is thus also to provide a method of adjusting the particle density in a suspension output from a microsystem for metering of the suspension output. Additional objects of this invention include providing microparticles and treating a microparticle flow that has been output.

The basic idea of this invention consists of creating a method of discharging a fluid flow with suspended microparticles from a fluidic microsystem in which the fluid flow is combined with at least one output flow at the end of an output channel of the microsystem to form a discharge flow which is then discharged as a total flow. In contrast with the conventional techniques of hydrodynamic focusing and the flow switch, the discharge flow is formed after manipulation and/or characterization of the suspended microparticles in a microsystem without influencing the flow conditions in it.

The discharge flow is delivered through a suitable conduction element (e.g., tubing, pipeline or the like) with characteristic dimensions which are adapted to the parameters of a component to accommodate the discharge flow (e.g., a measurement, storage or manipulator device).

The method of discharging the fluid flow is a metering (dosing) method in which the density of the microparticles and their provision at the end of the conduction element are adjusted in a predetermined manner. This invention makes it possible for the first time to adjust the velocities of flow required in operation of a fluidic microsystem freely and independently of one another. In the microsystem, there is a relatively low flow velocity of the microparticle suspension (see above). After output from the microsystem, the flow velocity should be increased in a certain manner, depending on the application. In contrast with the enveloping flow principle of hydrodynamic focusing, the velocities of flow of the fluid flow and the output flow have comparable values. The flow velocity of the output flow may be lower than, the same as or greater than the flow velocity of the fluid flow. However, no such great differences in velocity are established as in focusing (e.g., factor off a few thousand or more). In typical applications, the quotient of the velocities of flow of the fluid flows and output flows is in the range of 0.1 to 500, preferably less than 300. The inertia of the suspension dosage according to this invention in such flow ratios is preferably especially low. The particle-free volume of the output flow is adjustable individually especially after each individual microparticle has passed by with the fluid flow. The particle sequence in the fluid flow typically includes one microparticle in a time range of approx. 100 ms to 1 s. Such time ranges make it possible to adjust the flow velocity of at least one output flow. Depending on the task involved, individual particles can be removed from the microsystem more quickly or more slowly. Thus, a problem in microsystem technology which has been unsolved in the past has now been solved for the first time.

To produce the output flow, according to a preferred embodiment of this invention, a flow output device having at least one output channel is used, opening at the end of the discharge channel of the microsystem. Preferably several output channels are used, these channels being guided from different directions to the fluid flow. The most important object of the at least one output flow consists of the fluidic addition of a predetermined amount of liquid to the fluid flow at the end of the microsystem. By adjusting the flow rate of the output flow (volume throughput per unit of time) the specimen volume at the outlet of the microsystem can be adjusted as desired. Preferably at least one output flow is formed, its flow velocity being lower than the flow velocity of the fluid flow and its pump rate being greater than the pump rate of the fluid flow. According to this invention, a dilution of the fluid flow is provided at the outlet of the microsystem.

According to another function, the at least one output flow also serves to treat the suspended microparticles. To do so, the output flow is formed by at least one treatment solution, e.g., a washing solution, a culture medium or a conservative solution. Preferably multiple output channels are provided for guiding various treatment solutions from various directions which are combined with the fluid flow at the same time or successively downstream.

In an alternative embodiment of this invention, the pump rate of the output flow is adjusted so that its flow velocity has a defined value and is greater than the flow velocity of the fluid flow. In this embodiment, the flow output device itself may be used as a pump device for adjusting the flow conditions in the microsystem, replacing or relieving the pump devices in the channel arrangement of the microsystem.

An object of this invention is also a fluidic microsystem having a channel arrangement for receiving and/or flow-through of fluids with suspended microparticles and at least one discharge channel for guiding a fluid flow in which at least one flow output device having at least one output channel for guiding an output flow, opening at the end of the discharge channel, is provided at the end of the discharge channel.

The mouth of the at least one output channel at the end of the microsystem discharge is preferably designed so that the fluid flows and output flows converge. A conduction element, e.g., in the form of a tube or a pipe at the end of which may be provided at least one additional flow output device having additional output channels for further dilution of the discharge flow, is connected at the downstream end of the flow output device.

According to a preferred embodiment of the microsystem, the at least one output channel forms a side influx which opens into the discharge channel or at the end of the discharge channel. Since there is no focusing of particles, it is possible with advantage to omit the ring-shaped influx which is formed in hydrodynamic focusing and instead to provide a planar embodiment of the channel structure. There are advantages in particular with respect to the simple design and miniaturizability of the flow output device. When multiple output channels are provided, they are preferably also arranged in one plane as lateral influxes. Several flow output devices can also be arranged asymmetrically and/or offset with a distance from one another in the direction of flow, depending on their tasks.

According to another embodiment of this invention, the microsystem is equipped with a measurement or storage device arranged at the flow output device of the microsystem. A titer plate or a cell culture plate, for example is provided as the storage device.

A subject of this invention is also a flow output device for discharging suspended microparticles per se, which can be placed at an outlet of a fluidic microsystem for flow dilution of the fluid flow coming out. Flow dilution is understood to refer to the reduction in particle density in the fluid flow running during the flow by combining it with one or more output flows.

An important feature of this invention is that the dosage of the output fluid flow is based on the manipulation and/or characterization of the microparticles in the microsystem. In contrast with all conventional enveloping flow techniques, manipulation and/or characterization, such as dielectrophoretic treatments using dielectric field cages or field barriers, displacements or measurements with optical forces (optical tweezers), electrophoretic or electro-osmotic processes take place before the fluid flow converges with the at least one output flow. For example, first the microparticles are separated spatially using essentially known field barriers and are worked up in the channel arrangement of the microsystem. The microparticles are measured at the respective positions. Releasing the field barriers causes the microparticles to be removed through the discharge channel with the flow velocity in the channel arrangement, i.e., at a relatively low transport velocity. Although the low transport velocity is desirable in the microsystem, e.g., to fill up the dielectric field cages, the transport velocity (flow velocity) established in the flow output device is elevated, depending on the application. Due to the output flow supplied, it is advantageously ensured that the microparticles tested in a separated state will still remain separated even after manipulation or measurement, with no losses occurring and short transport times being achieved.

This offers special advantages in manipulation of biological cells and especially in depositing of single cells.

This invention offers the following advantages. Due to the use of an output flow at the outlet of a microsystem, the suspended microparticles, e.g., biological cells or cell constituents, synthetic particles or composite particles with biological and synthetic components, macromolecules or aggregates of macromolecules can be removed from the microsystem with little or no loss. The flow rate in the output flow can be increased without any interfering influence on the flow velocity in the microsystem upstream from its outlet. Due to the increase in the flow velocity of the particle suspension after discharge from the microsystem, the risk of interactions between the particles and the channel walls is reduced. For example, cell adhesion can be prevented. This invention is applicable to advantage especially at low velocities of flow in the microsystem in the range of 1 μm/s to 10 mm/s, for example. According to this invention, the velocity of the particle suspension in discharge from the microsystem can be increased as greatly as possible for effective and rapid discharge of the particles from the microsystem. For example, a peristaltic pump is suitable for this purpose. In one example, the velocity of the suspension could be accelerated from 1-20 μl/h to 70 to 280 μl/h. At higher velocities of flow, however, pulsation of the peristaltic pump acts on the flow of the particles upstream from the flow output device (e.g., disturbance in maintaining the microparticles in dielectric field cages).

Use of a hydrodynamic pump principle is more suitable for rapid discharge of the particles. For example, the liquid may be sent to the flow output device from a liquid-filled reservoir which is acted upon at a low excess pressure applied via a compressor with a throttle valve connected to it. Thus, much higher flow rates, namely up to 25 μl/s (with a working range of up to 0.8 bar excess pressure), or typically 2 μl/s (with a working range of up to 0.1 bar excess pressure) can be achieved in the microsystem without any negative effect on the incoming particle suspension.

However, there is also a reduction in the suspension density. This reduction in suspension density is to be differentiated from the particle alignment in hydrodynamic focusing. After manipulation and/or characterization of individual microparticles in the microsystem, they are already aligned in a row at the outlet or otherwise separated. However, the reduction in suspension density means that fluid quantities containing one or a few particles, e.g., in the form of drops, can be provided, such that their volume is adapted to the receiving volume of a connected measuring device. A predetermined drop size may be formed at the end of the conduction element downstream from the flow output device, which is advantageous for single-cell deposition.

A reduction in suspension density also permits more generous tolerances in fluid coupling. When dead volumes develop in the discharge flow in particle manipulation in the microsystem, e.g., as a result of sorting processes, they are compensated by the dilution of the suspension.

Another important advantage is in the addition of treatment solutions to the fluid flow. The treatment solution may be used with a much greater volume in comparison with the suspension volume in the microsystem. Different output flows may consist to advantage of different treatment solutions and may optionally be supplied at different flow rates. The treatment of the microparticles discharged can be adjusted quantitatively.

The flow output device according to this invention can be adapted easily to any microsystems because there are no restrictions with regard to the geometry of the convergence of the fluid flow and the output flow. In particular, it is not absolutely necessary for the fluid flow to be completely enveloped by the output flow. Also, no focusing of the microparticles in the discharge flow is necessary.

To achieve the flow dilution according to this invention, the flow velocity of the output flow can be set so low with a suitable cross section of the output channel so that essentially there is no feedback effect on the microsystem.

This invention can also be used with microsystems in which there is no net flow in the microsystem or it is negligible, and the microparticles are moved through the channel arrangement by electric or magnetic forces.

BRIEF DESCRIPTION OF SEVERAL VIEWS OF THE DRAWINGS

Additional details and advantages of this invention are described below with reference to the drawings, which show.

DETAILED DESCRIPTION OF THE INVENTION

Figure 1:
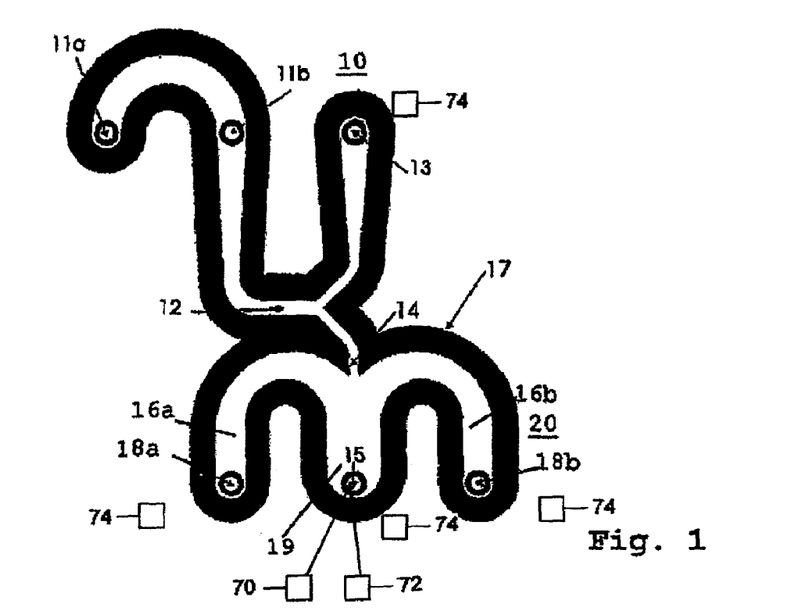
FIG. 1 an embodiment of a microsystem according to this invention equipped with a flow output device.

FIG. 1 illustrates in a schematic top view components of a fluidic microsystem 10 having a flow output device 20 which is designed for implementation of the discharge of suspended microparticles from the microsystem by the method according to this invention. The term fluidic microsystem is understood to refer here in general to a device having at least one input, one channel arrangement for receiving and/or guiding a fluid, in particular a particle suspension, and at least one outlet. Liquid lines extending through the channel arrangement between the inlets and outlets have geometric designs, dimensions and cross-sectional shapes depending on application. The liquid lines are designed, for example, as structured channels in a solid-state carrier (chip), e.g., made of a semiconductor material or a plastic. The channel bottoms are formed by the chip material and the channel covers are formed by a suitable chip cover, e.g., made of glass or plastic. However, it is also possible for the side walls of the channel to be formed by spacers which are suitably shaped and project from a solid-state carrier. Furthermore, microelectrodes may be provided in the fluidic microsystem to form high-frequency electric fields for dielectrophoretic manipulation of the particles, and manipulation devices such as electroporation electrodes, pump devices and measuring devices may also be provided. These components are known per se from microsystems technology and therefore need not be explained in detail here.

Typical dimensions of the channel arrangement of the microsystem are less than 800 μm, preferably 500 μm (channel width) and less than 200 μm (channel height).

In the embodiment of this invention illustrated in FIG. 1, the fluidic microsystem 10 and the flow output device 20 are provided together on a substrate through a spacer 17 forming the channel walls. As an alternative, it is also possible to design the microsystem 10 and the flow output device 20 separately from one another as modular units (see below).

The microsystem 10 has two inlets 11a and 11b which are connected to a main channel 12, which generally represents a system function-specific channel arrangement. The main channel 12 is divided at the end into a drain 13 (so-called waste channel) for discharging unwanted or separated fluid and/or microparticle components and a discharge channel 14. The suspension with the desired microparticles, which are to be transferred from the microsystem to a connected component for receiving the output flow, e.g., a measurement unit 70, storage unit or manipulation unit 72, is guided in discharge channel 14. Therefore, the flow output device 20 is provided at the end of the discharge channel 14.

The flow output device 20 has two output channels 16a, 16b, each extending from an output flow inlet 18a, 18b to the end of the discharge channel 14. The output channels 16a, 16b open at the end of the discharge channel 14 in such a way that the respective directions of flow in the discharge and output channels form an angle smaller than 90°. After the mouth, the output channels 16a, 16b develop into a conduction element 19 which ends at an outlet 15. The arrangement of output channels 16a, 16b, which is also known as a double-horn arrangement, is characterized by a mirror-symmetrical arrangement of the curved output channels 16a, 16b with respect to the lengthened direction of flow at the end of the discharge channel 14.

The channel structure 10, 20 is also equipped with pump devices 74, which ensure a fluid transport in the microsystem 10, discharge of unwanted fluid through the drain 13, transport of output flows through output channels 16a, 16b and discharge of the discharge flow formed from the output and discharge flows through conduction element 19 to outlet 15. These pump devices 74 are know per se and include, for example, peristaltic pumps, spray pumps or electro-osmotically active fluid or particle drives. Further examples include pump devices based on hydrostatic pressure.

The channels in the microsystem according to this invention typically have channel heights of approx. 20 to 50 µm and channel widths of approx. 200 to 800 µm. The set velocities of flow in the channels are preferably in the range of 50 to 1000 µm/s, corresponding to a pump rate in the range of 1 to 20 µl/h. The output channels 16a, 16b have larger cross-sectional dimensions than discharge channel 14. The channel width is typically in the range of 5 µm to 500 µm.

Microsystem 10 according to FIG. 1 is operated as follows. The microsystem 10 is used, for example, to separate suspended microparticles as a function of their ability to react to a certain substance influence (e.g., an antibody). A fluid with the microparticles to be separated or a solution with an active ingredient is added through the inlets 11a, 11b. In the main channel 12, there occur an interaction between the microparticles and the active ingredient and the actual separation operation. The separation operation includes, for example, the following steps. First, the microparticles are separated and aligned by using field barriers which are known as such. Then a measurement is performed on the individual microparticles, e.g., a measurement of the dielectric rotation. Depending on the result of the measurement, a field barrier at the end of the main channel 12 is confirmed to deflect the microparticles into the drain 13 or the discharge channel 14. In discharge of the microparticles from the discharge channel 14, with the traditional systems there is the problem that the transport velocity remains unchanged at a low level; this problem is solved here by operation of the flow output device 20.

In the flow output device 20, in the output channels 16a, 16b, from the inlets 18a, 18b to the end of the discharge channel 14 output flows are made to flow at a higher pump rate in comparison with the fluid flow in the discharge channel 14. The fluid flow is merged with the output flows to form a discharge flow. The discharge flow conveys the microparticles from the discharge channel 14 to the outlet 15 of the conduction element 19. Due to the output flows thus supplied, adhesion of microparticles to the edge of the conduction element 19 and their sedimentation are prevented. Microparticles arriving at the end of the discharge channel 14 are conveyed reliably and at a predetermined velocity to outlet 15. This facilitates in particular the deposition of microparticles in the reservoirs of a cell culture plate.

An additional tubing or hosing element in which the entire discharge flow composed of fluid flow and output flow is conveyed can be connected to the outlet 15 of the flow output device 20 without the aforementioned adhesion or sedimentation problems occurring.

The entire discharge flow composed of fluid flow and output flow is supplied with a defined suspension density. Quantities of fluid having one or more particles, e.g., in the form of drops, leave at the outlet of the output device or the tubing element. The volumes of these fluid quantities can be adjusted to the requirements of a downstream measurement or storage device with the flow output device. For example, the fluid quantities (drops) are separated and deposited on a titer plate of a high-throughput screening system. Single-cell separation is preferably achieved. As an alternative, the cells may also be separated and deposited on a cell culture plate as the storage device.

Figure 2:
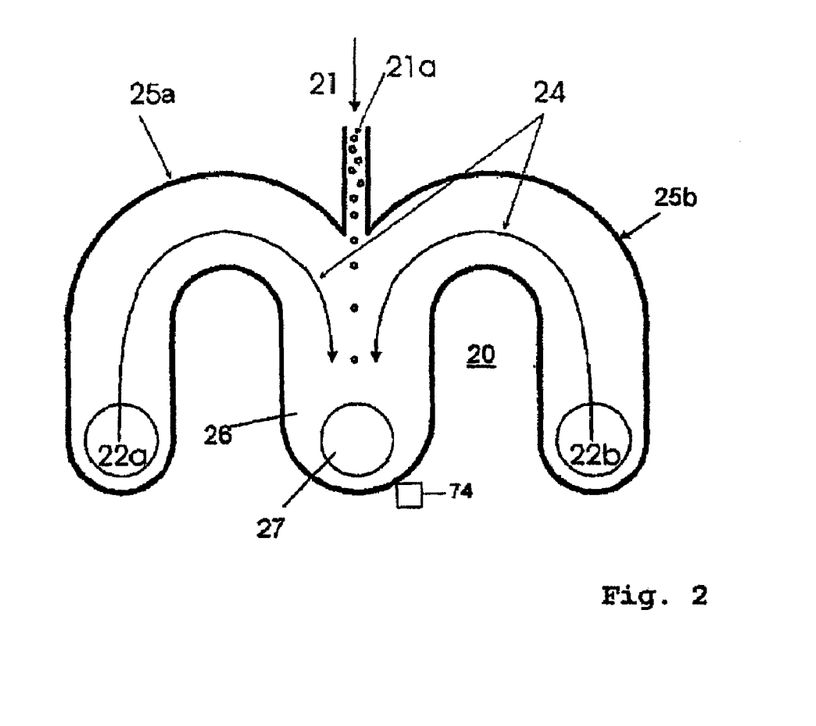
FIG. 2 a top view of a flow output device according to this invention.

FIG. 2 shows another embodiment of the flow output device 20 in the "double-horn"-arrangement. In the discharge channel 21 of the microsystem 10 (not shown here), microparticles 21a are transported in the direction of the arrow. Output flows 24 flow according to the direction of the arrow shown here from the output flow inlets 22a, 22b through the output channels 25a, 25b opening at the end of the discharge channel 21. The output flows 24 are generated with a peristaltic pump, a spray pump or a pump device based on hydrostatic pressure. They entrain the particles 21a at the end of the discharge channel so that they are guided to the outlet 27 through the conduction element 26. The outlet 27 of the flow output device 20 is preferably arranged at the point of intersection of the converging output flows 24. In the symmetrical channel alignment, this corresponds to a position on a reference line which corresponds to the alignment of the discharge channel 21.

Figure 3:
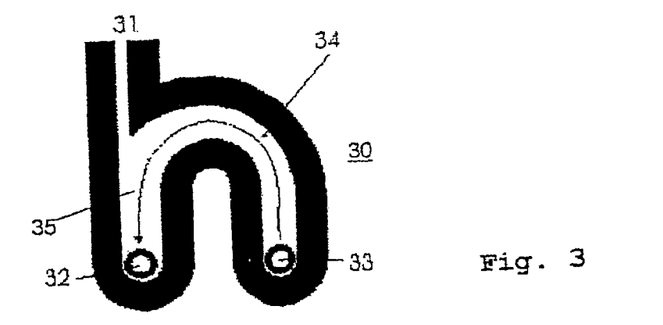
FIGS. 3, 4, 5 and 6 top views of other embodiments of a flow output device according to this invention.

FIG. 3 shows a modified embodiment of the flow output device according to this invention. The flow output device 30 at the end of the discharge channel 31 has only one output channel 34 leading from an inlet 33 to the outlet 32 of the conduction element 35. As in the embodiments described above, the fluid flow from the discharge channel 31 also converges with the output flow in the output channel 34 in this asymmetrical design. The microparticles contained in the fluid flow are entrained in the common discharge flow and lead to the outlet 32. It has surprisingly been found that even with this asymmetrical design, adherence of microparticles to the wall of the conduction element 35 is prevented.

Figure 4:
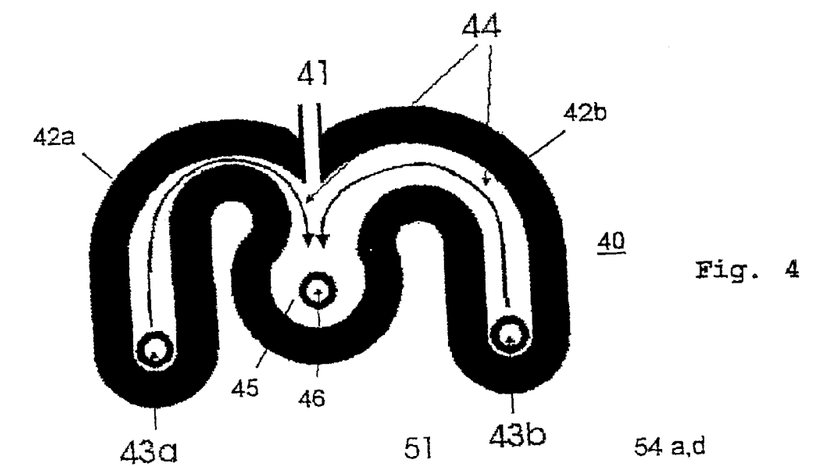

FIG. 4 illustrates another example of a "double-horn"-arrangement, although in contrast with the embodiment according to FIG. 2, this one has an asymmetrical design. The flow output device 40 at the end of the discharge channel 41 has a first output channel 42a with a narrow channel cross section and a second output channel 42b with a wide channel cross section leading from inputs 43a, 43b to outlet 46 via conduction element 45, respectively.

Reference number 44 denotes the output flows which are formed asymmetrically with respect to the pump rates and the geometry of the convergence with the fluid flow from the discharge channel 41.

Due to the asymmetrical design according to FIG. 4, the inflow of certain treatment substances is further modified with the output flows 44, as is also possible in the embodiments explained above, with respect to the substance quantities or directions of inflow of the output flow. For example, the quantity of treatment substance added to one output flow can be varied as a function of the measurement or operating state of the microsystem 10 (see FIG. 1).

Figure 5:
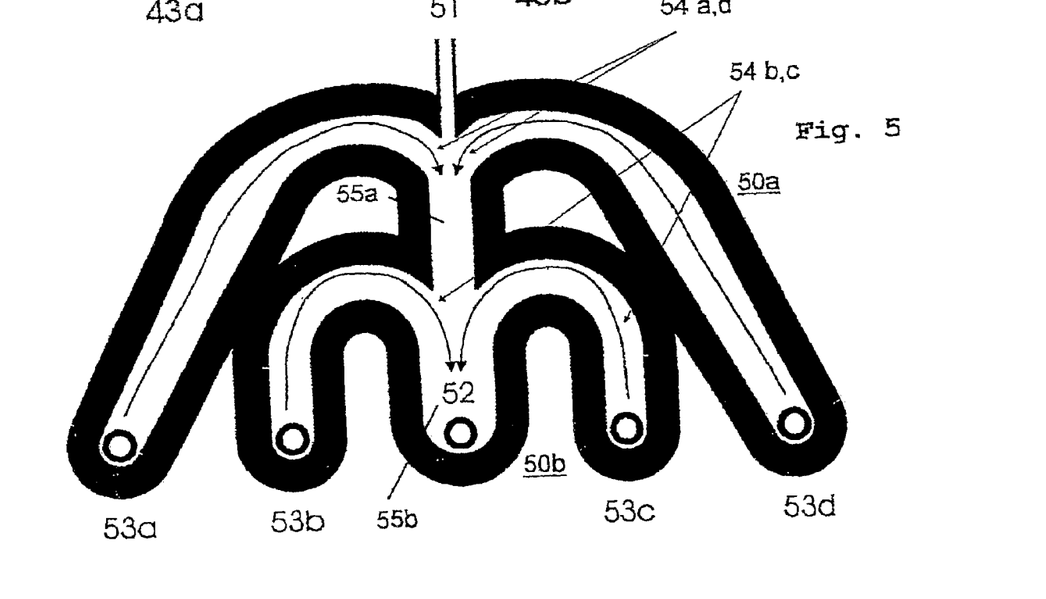

FIG. 5 illustrates another embodiment of this invention in a schematic top view in which two series-connected flow output devices 50*a*, 50*b* are provided. The flow output devices 50*a*, 50*b* are situated one after the other in the direction of flow. The first flow output device 50*a* is situated at the end of the discharge channel 51 and is provided with the inputs 53*a*, 53*d* and the curved output channels for guiding the output flows 54*a*, 54*d*. The second flow output device 50*b* is mounted at the outlet of the conduction element 55*a*. The second flow output device 50*b* also includes curved output channels from inlets 53*b*, 53*c* to guide the output flows 54*b*, 54*c*. The output flow formed from the fluid flow and the output flows is delivered via the outlet 52.

In the embodiment according to FIG. 5, various treatment solutions, culture media or conservative solutions may be supplied through the individual output channels. The design according to FIG. 5 may also be asymmetrical or through modified opening of the output channels. The output channels may be provided, for example, according to certain positions on conduction elements 55*a*, 55*b* to supply the treatment solutions according to a defined protocol.

Figure 6:
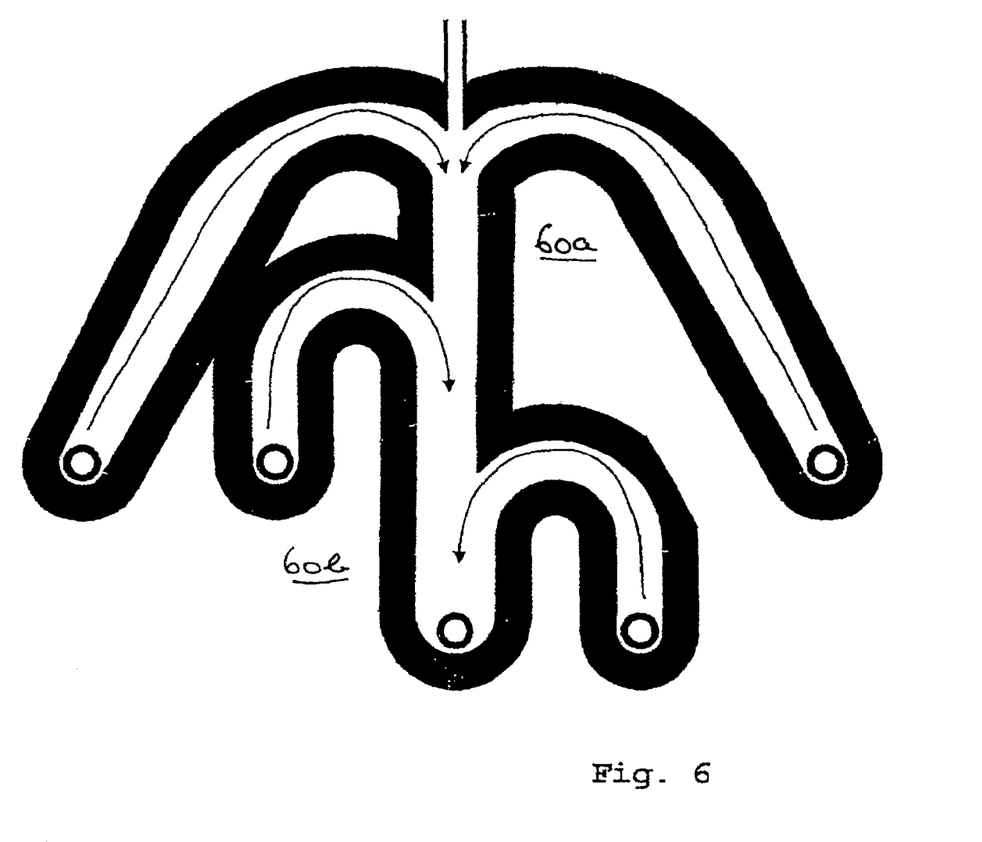

FIG. 6 shows an example of modification of the opening of the output channels. By analogy with FIG. 5, two series-connected flow output devices 60*a*, 60*b* are provided, the first having two output channels arranged in the same position with respect to the direction of flow. In the case of the second flow output device 60*b*, the output channels are arranged so they are offset relative to one another in the direction of flow. The distance between the lateral influxes is in the µm to mm range, for example.

A channel structure for implementation of this invention may be modified in a variety of ways in comparison with the embodiments explained above. For example, a flow output device for discharging suspended microparticles may be provided as a separate component, the device being mounted on the discharge channel (e.g., 14, see FIG. 1) of a microsystem. A flow output device has dimensions of approx. 1 to 20 mm and can thus easily be set up manually without requiring suitable means, e.g., tweezers. For example, sealed connectors made of plastic or the like may be provided for the connection between the flow output device component and a microsystem chip.

In deviation from the shape of curved output channels illustrated here, other straight or curved channel designs may also be provided. The output flows may also disembogue at the end of the respective discharge channel in a plane different from the fluidic microsystem. In the case of microsystems having multiple output channels or at the end of the outlet of a microsystem, flow output devices according to this invention may also be mounted. Additional possible modifications are derived with respect to the size and the flow parameters of the flow output device, depending on the application.

According to this invention, with the embodiments described above, it is possible for additional devices for particle and/or fluid manipulation to be arranged in the conduction element of a flow output device (e.g., conduction element 19 in FIG. 1). These devices include, for example, additional electrodes for developing electric fields in the suspension flow in the conduction element. Electroosmotic flows can be induced or electrophoretic particle separation can be performed in an essentially known way with the electric fields. In such embodiments, instead of one outlet (e.g., outlet 15 in FIG. 1) several outlets may also be provided as discharge elements for separated particles and/or flows at the end of a conduction element.

The features of this invention disclosed in the preceding description, as illustrated in the drawing and characterized in the claims may be relevant either individually or in any desired combination for implementation of the invention in its various embodiments.

The invention claimed is:

1. A fluidic microsystem comprising:
    a channel arrangement, which comprises liquid lines for receipt and/or continuous flowing of a suspension fluid containing suspended microparticles, a manipulation device for a manipulation of the suspended microparticles and a measuring device for a characterization of the suspended microparticles, said manipulation device including at least one of dielectric field cages and field barriers for a dielectrophoretic treatment of the suspended microparticles;
    a discharge channel adapted to guide the suspension fluid, the discharge channel being connected with a downstream end of the channel arrangement; and
    at least one flow output device for producing at least one output flow of a liquid to be added to the fluid flow, said at least one flow output device having at least one output channel for guiding said at least one output flow,
    the at least one output channel having a larger cross-sectional dimension than the discharge channel,
    the at least one output channel including a section having a longitudinally curved shape that opens out as a side influx at a mouth coupled to an end of the discharge channel at an acute angle,
    the at least one flow output device including a pump device with a controllable pump rate, the pump device being connected with the at least one output channel to adjust the at least one output flow independently of the suspension fluid flow in the liquid lines of the channel arrangement,
    the at least one output channel and the discharge channel converging into a conduction element which ends at an outlet of the fluidic microsystem, the conduction element being arranged for guiding a discharge flow composed of the suspension fluid and at least one output flow to the outlet,
    the at least one output channel opening at the end of the discharge channel and adapted for guiding the output flow with the respective flow directions of the output flow in the corresponding output channel and the suspension fluid in the discharge channel running at the mouth of the at least one output channel into the end of the discharge channel at an angle of less than 90° to one another.

2. The microsystem according to claim 1, wherein several flow output devices are positioned adjacent to each other, wherein each of the flow output devices has at least one output channel which opens out at the end of the discharge channel or on the conduction element.

3. The microsystem according to claim 1, wherein one single output channel is provided opening into the end of the discharge channel at a first side of the discharge channel.

4. The microsystem according to claim 1, wherein two output channels are provided opening into the end of the discharge channel at a first side and a second side of the discharge channel, wherein the first and second sides are opposite to each other.

5. The microsystem according to claim 4, wherein the two output channels form channel arcs being shaped asymmetrically relative to the discharge channel.

6. The microsystem according to claim 1, wherein the pump device is adapted for generating hydrostatic pressure.

7. The microsystem according to claim 1, wherein the at least one flow output device has at least one reservoir for accommodating at least one treatment solution forming the at least one output flow.

8. The microsystem according to claim 7, wherein the at least one treatment solution includes at least one member selected from the group consisting of a washing solution, a conservative solution, a culture medium and a cryoconservation solution.

9. The microsystem according to claim 1, wherein the channel arrangement is part of a solid-state chip to which the flow output device is detachably attached.

* * * * *